(12) United States Patent
Yamamoto et al.

(10) Patent No.: US 12,334,223 B2
(45) Date of Patent: Jun. 17, 2025

(54) LEARNING APPARATUS, MENTAL STATE SEQUENCE PREDICTION APPARATUS, LEARNING METHOD, MENTAL STATE SEQUENCE PREDICTION METHOD AND PROGRAM

(71) Applicant: NIPPON TELEGRAPH AND TELEPHONE CORPORATION, Tokyo (JP)

(72) Inventors: Shuhei Yamamoto, Tokyo (JP); Hiroyuki Toda, Tokyo (JP); Takeshi Kurashima, Tokyo (JP); Tomu Tominaga, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 77 days.

(21) Appl. No.: 18/245,965

(22) PCT Filed: Nov. 12, 2020

(86) PCT No.: PCT/JP2020/042295
§ 371 (c)(1),
(2) Date: Mar. 20, 2023

(87) PCT Pub. No.: WO2022/102060
PCT Pub. Date: May 19, 2022

(65) Prior Publication Data
US 2023/0368920 A1   Nov. 16, 2023

(51) Int. Cl.
*G16H 50/20* (2018.01)
*G16H 20/70* (2018.01)

(52) U.S. Cl.
CPC ............. *G16H 50/20* (2018.01); *G16H 20/70* (2018.01)

(58) Field of Classification Search
CPC ...... G16H 10/60; G16H 50/20; A61B 5/4803; A61B 5/1126
(Continued)

(56) References Cited

U.S. PATENT DOCUMENTS

| 7,917,302 B2* | 3/2011 | Rognes | G16B 30/10 |
| | | | 435/6.13 |
| 11,302,448 B1* | 4/2022 | Jain | G16H 10/60 |

(Continued)

FOREIGN PATENT DOCUMENTS

| CN | 101460625 A | * | 6/2009 | ........... C07K 14/775 |
| CN | 111419249 B | * | 4/2023 | .............. A61B 5/024 |

OTHER PUBLICATIONS

Decoding Spontaneous Emotional States in the Human Brain, Philip A. Kragel, Annchen R. Knodt, Ahmad R. Hariri, Kevin S. LaBar, Published: Sep. 14, 2016, PLOSBiology (Year: 2016).*

(Continued)

*Primary Examiner* — Dilek B Cobanoglu
(74) *Attorney, Agent, or Firm* — IPUSA, PLLC

(57) ABSTRACT

A learning device includes: a psychological state data preprocessing unit that calculates a duration of a psychological state from psychological state sequence data, and generates preprocessed psychological state sequence data including the psychological state and the duration; and a learning unit that learns a psychological state sequence prediction model, using input sequence data including behavior sequence data and the preprocessed psychological state sequence data, and correct sequence data that is preprocessed psychological state sequence data at a time later than the input sequence data.

8 Claims, 17 Drawing Sheets

(58) Field of Classification Search
USPC .......................................... 707/769; 705/2, 3
See application file for complete search history.

(56) References Cited

U.S. PATENT DOCUMENTS

| | | | | |
|---|---|---|---|---|
| 2014/0156698 | A1* | 6/2014 | Stivoric | G16H 50/20 707/769 |
| 2017/0258390 | A1* | 9/2017 | Howard | A61B 5/4803 |
| 2022/0000405 | A1* | 1/2022 | Tsuji | A61B 5/1126 |

OTHER PUBLICATIONS

Using Machine Learning and Smartphone and Smartwatch Data to Detect Emotional States and Transitions: Exploratory Study, Madeena Sultana1,2*, PhD; Majed Al-Jefri1,3*, PhD; Joon Lee1,2,3, PhD, JMIR MHealth and Unhealth, JMIR Mhealth Uhealth 2020 (Year: 2020).*

A Review of Emotion Recognition Methods Based on Data Acquired via Smartphone Sensors, Agata Kolakowska * , Wioleta Szwoch and Mariusz Szwoch, Sensors 2020 (Year: 2020).*

DeepMood: Forecasting Depressed Mood Based on Self-Reported Histories via Recurrent Neural Networks, 2017 International World Wide Web Conference Committee (IW3C2), published under Creative Commons CC BY 4.0 License. WWW2017, Apr. 3-7, 2017, Perth, Australia. ACM978-1-4503-4913-0/17/04, Suhara et al. (Year: 2017).*

E. Nosakhare and R. Picard: Probabilistic Latent Variable Modeling for Assessing Behavioral Influences on Well-Being. In Proc. of KDD, 2019.

S. Yan et al.: Estimating Individualized Daily Self-Reported Affect with Wearable Sensors. In Proc. of ICHI, 2019.

D. Spathis, S. Servia-Rodriguez, K. Farrahi, C. Mascolo, and J. Rentflow: Sequence Multi-task Learning to Forecast Mental Well-being from Sparse Self-reported Data. In Proc. of KDD, 2019.

J.P. Pollak, P. Adams, G. Gay: PAM: A Photographic Affect Meter for Frequent, In Situ Measurement of Affect. In Proc. of CHI, 2011.

* cited by examiner

Fig. 5

| DATA ID | DATE AND TIME | NUMBER OF STEPS | EXERCISE TIME | CONVERSATION TIME | ..... |
|---|---|---|---|---|---|
| 1 | 2020/03/01 07:00 | 3000 | 30 min | 0 min | ..... |
| 2 | 2020/03/01 08:00 | 100 | 0 min | 50 min | ..... |
| 3 | 2020/03/01 09:00 | 200 | 0 min | 10 min | ..... |
| 4 | ..... | ..... | ..... | ..... | ..... |
| 5 | ..... | ..... | ..... | ..... | ..... |
| 6 | ..... | ..... | ..... | ..... | ..... |

Fig. 6

| DATA ID | DATE AND TIME | NUMBER OF STEPS | EXERCISE TIME | CONVERSATION TIME | ..... |
|---|---|---|---|---|---|
| 1 | 2020/03/01 07:00 | 0.5 | 0.1 | 0.0 | ..... |
| 2 | 2020/03/01 08:00 | -1.2 | 0.0 | 0.9 | ..... |
| 3 | 2020/03/01 09:00 | 1.0 | 0.3 | 0.2 | ..... |
| 4 | ..... | ..... | ..... | ..... | ..... |
| 5 | ..... | ..... | ..... | ..... | ..... |
| 6 | ..... | ..... | ..... | ..... | ..... |

Fig. 7

| DATA ID | DATE AND TIME | Valence | Arousal |
|---|---|---|---|
| 1 | 2020/03/01 07:00 | 1.5 | 2.2 |
| 2 | 2020/03/01 20:00 | 3.3 | 4.5 |
| 3 | 2020/03/01 23:00 | 1.1 | -2.1 |
| 4 | ...... | ...... | ...... |
| 5 | ...... | ...... | ...... |
| 6 | ...... | ...... | ...... |

Fig. 8

| DATA ID | DATE AND TIME | Valence | Arousal | DURATION |
|---|---|---|---|---|
| 1 | 2020/03/01 07:00 | 1.5 | 2.2 | 3.0h |
| 2 | 2020/03/01 20:00 | 3.3 | 4.5 | 3.0h |
| 3 | 2020/03/01 23:00 | 1.1 | −2.1 | 8.0h |
| 4 | ..... | ..... | ..... | ..... |
| 5 | ..... | ..... | ..... | ..... |
| 6 | ..... | ..... | ..... | ..... |

Fig. 15

| PARAMETER NAME | PARAMETER VALUE |
|---|---|
| FULLY CONNECTED LAYERS 1, 2, 3, 4 | $\begin{bmatrix} 0.1 & \cdots & 0.3 \\ \vdots & \ddots & \vdots \\ 0.2 & \cdots & 0.1 \end{bmatrix} \cdots$ |
| RNNs 1, 2, 3 | $\begin{bmatrix} 0.1 & \cdots & 0.3 \\ \vdots & \ddots & \vdots \\ 0.2 & \cdots & 0.1 \end{bmatrix} \cdots$ |
| OUTPUT LAYER (MEAN VALUE) | $\begin{array}{ccc} \mu_{v,k} & \mu_{a,k} & \mu_{d,k} \end{array}$ $\begin{bmatrix} 0.1 & 0.5 & 0.3 \\ \vdots & \vdots & \vdots \\ 0.2 & -0.4 & 0.1 \end{bmatrix}$ |
| OUTPUT LAYER (VARIANCE) | $\begin{array}{ccc} \sigma_{v,k} & \sigma_{a,k} & \sigma_{d,k} \end{array}$ $\begin{bmatrix} 0.2 & 0.5 & 0.5 \\ \vdots & \vdots & \vdots \\ 0.1 & 0.8 & 0.8 \end{bmatrix}$ |
| OUTPUT LAYER (CORRELATION) | $\begin{array}{ccc} \rho_{va,k} & \rho_{vd,k} & \rho_{ad,k} \end{array}$ $\begin{bmatrix} 0.25 & 0.5 & 0.3 \\ \vdots & \vdots & \vdots \\ 0.2 & -0.4 & 0.1 \end{bmatrix}$ |

LEARNING APPARATUS, MENTAL STATE SEQUENCE PREDICTION APPARATUS, LEARNING METHOD, MENTAL STATE SEQUENCE PREDICTION METHOD AND PROGRAM

TECHNICAL FIELD

The present invention relates to a technology for predicting psychological states, and particularly to a technology for enabling an accurate automatic prediction of a future psychological state (mood) sequence of a user from past behavior data and a past psychological state sequence of the user.

BACKGROUND ART

With the spread of wearable sensors such as smartwatches, fitness trackers, and smartphones, it has become possible to easily record a user's biological information and behavior logs (hereinafter referred to as behavior data). Detailed analysis of such behavior data and psychological states (such as moods, emotions, stress levels) obtained through the user's self-evaluation can be used for various purposes.

For example, if the today's stress level can be estimated as a numerical value or a future mood can be predicted with the use of a user's behavior data history acquired through a smartwatch, the obtained result can be used for various purposes such as recommendation of a behavior effective for improving the psychological state of the user.

As a technology for automatically estimating a psychological state of a user from such behavior data, there is a conventional technology by which obtained data is discretized and converted into a histogram, and a health level and a stress level are estimated by a probabilistic generation model (Non Patent Literature 1). There also is a technology by which a psychological state of the next day is returned with the use of daily sequence data of operation logs and screen times acquired through a smartphone (Non Patent Literature 2).

CITATION LIST

Non Patent Literature

Non Patent Literature 1: E. Nosakhare and R. Picard: Probabilistic Latent Variable Modeling for Assessing Behavioral Influences on Well-Being. In Proc. of KDD, 2019.
Non Patent Literature 2: S. Yan et al.: Estimating Individualized Daily Self-Reported Affect with Wearable Sensors. In Proc. of ICHI, 2019.
Non Patent Literature 3: D. Spathis, S. Servia-Rodriguez, K. Farrahi, C. Mascolo, and J. Rentflow: Sequence Multi-task Learning to Forecast Mental Wellbeing from Sparse Self-reported Data. In Proc. of KDD, 2019.
Non Patent Literature 4: J. P. Pollak, P. Adams, G. Gay: PAM: A Photographic Affect Meter for Frequent, In Situ Measurement of Affect. In Proc. of CHI, 2011.

SUMMARY OF INVENTION

Technical Problem

However, by the above conventional methods, data is separated and statistically processed on a daily basis. Therefore, time-oriented fluctuations in the user's mood and emotion depending on dates and times cannot be taken into consideration. For example, by the technology disclosed in Non Patent Literature 2, mood data posted many times in one day is quantified and converted into a mean value, and the mean value of moods of the next day is then predicted. On the other hand, since a person's mood fluctuates even in one day, it is not possible to show the mood fluctuations to the user simply by predicting the mean value.

Further, by the technology disclosed in Non Patent Literature 3, a future mood data sequence is predicted from a past behavior data sequence. However, since it is unclear how long the predicted mood lasts, the time interval at which the user's mood fluctuates cannot be determined, and it is not possible to accurately estimate the influence of future mood fluctuations on mental health.

The present invention has been made in view of the above points, and aims to provide a technology for enabling prediction of future mood data, together with its duration, from past behavior data and mood data of the user.

Solution to Problem

The technology disclosed herein provides a learning device that includes:
  a psychological state data preprocessing unit that calculates a duration of a psychological state from psychological state sequence data, and generates preprocessed psychological state sequence data including the psychological state and the duration; and
  a learning unit that learns a psychological state sequence prediction model, using input sequence data including behavior sequence data and the preprocessed psychological state sequence data, and correct sequence data that is preprocessed psychological state sequence data at a time later than the input sequence data.

Advantageous Effects of Invention

According to the disclosed technology, it is possible to predict future mood data, together with its duration, from the user's past behavior data and mood data.

BRIEF DESCRIPTION OF DRAWINGS

FIG. 5 is a diagram illustrating an example of the storage format of a behavior sequence data DB.
FIG. 6 is a diagram illustrating an example of feature vector data obtained through processing by a feature amount extraction unit.
FIG. 7 is a diagram illustrating an example of the storage format of a mood sequence data DB.
FIG. 8 is a diagram illustrating an example of preprocessed mood data.

FIG. 15 is a diagram illustrating an example of the storage format of a mood sequence prediction model DB.

DESCRIPTION OF EMBODIMENTS

The following is a description of an embodiment (the present embodiment) of the present invention, with reference to the drawings. The embodiment described below is merely an example, and embodiments to which the present invention is applied are not limited to the following embodiment.

In view of the above-mentioned problems of the conventional technologies, the present embodiment concerns the configuration and operations of a psychological state sequence prediction device designed to be capable of predicting a user's future mood sequence, together with its duration time, on the basis of the past behavior data and mood data.

Example Configuration of a Device

Figure 1:
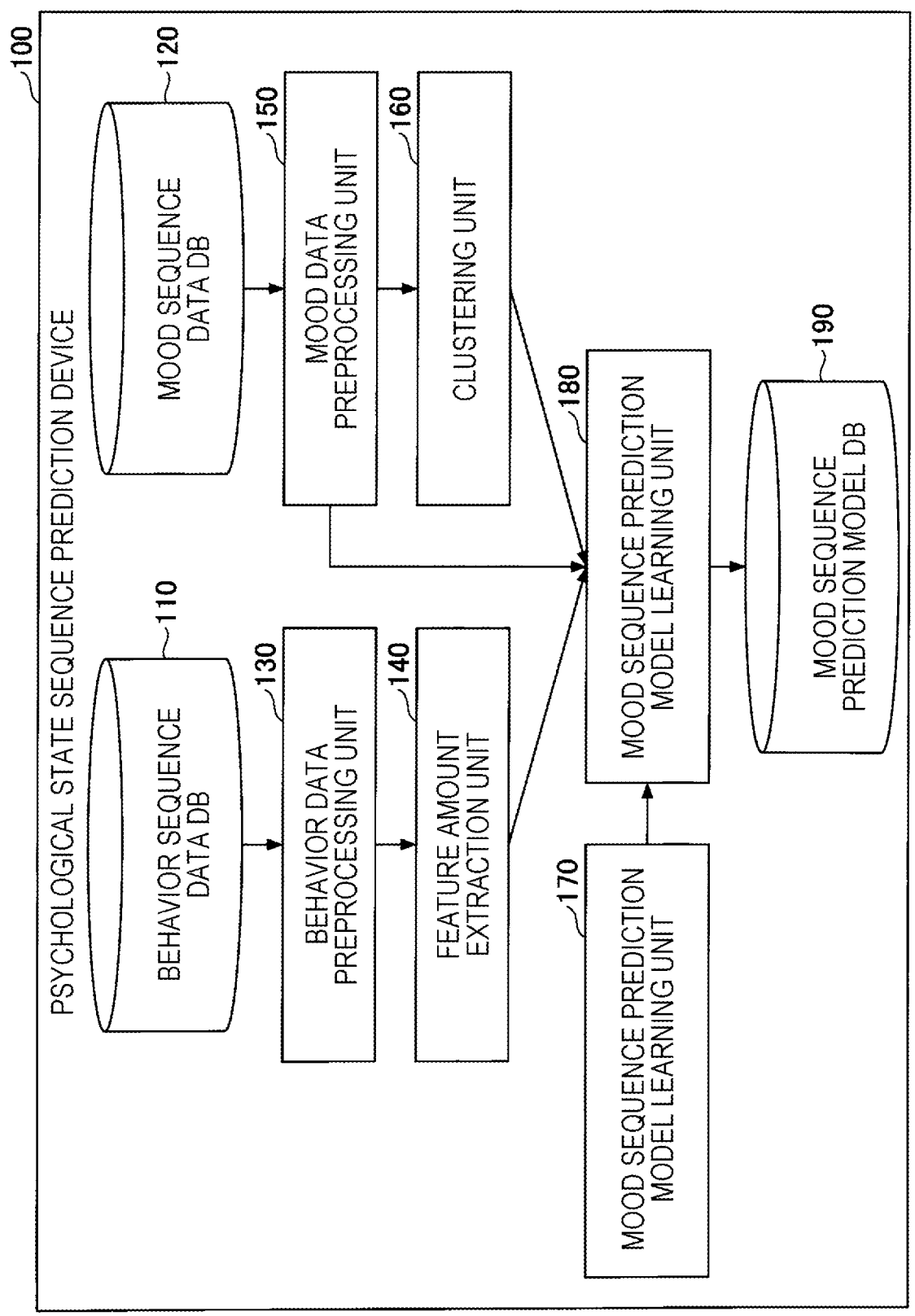
FIG. 1 is a configuration diagram of a psychological state sequence prediction device according to an embodiment of the present invention.
Figure 2:
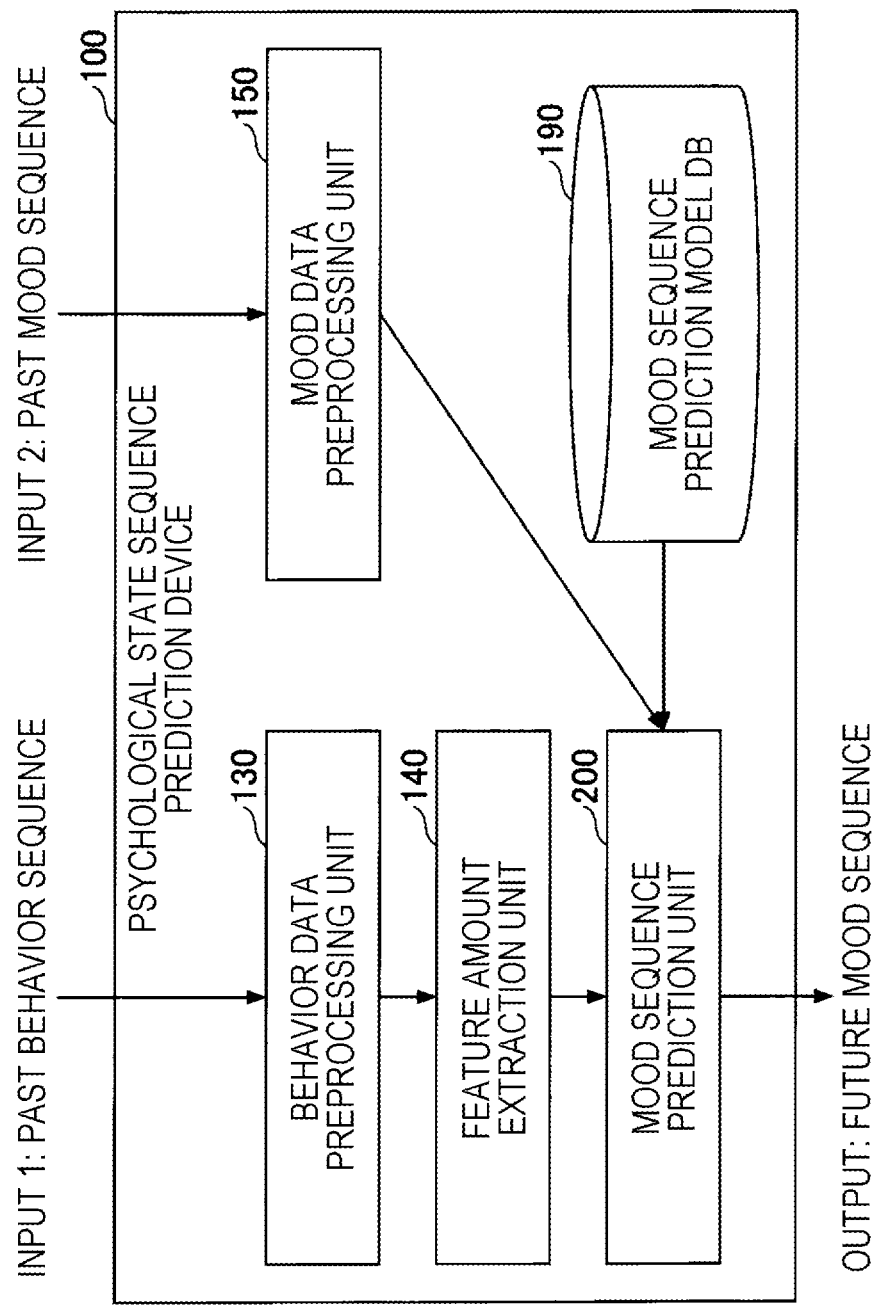
FIG. 2 is a configuration diagram of a psychological state sequence prediction device according to an embodiment of the present invention.

FIGS. 1 and 2 illustrate an example configuration of a psychological state sequence prediction device 100 according to the present embodiment. FIG. 1 illustrates a configuration in a learning phase, and FIG. 2 illustrates a configuration in a prediction phase. Note that the psychological state sequence prediction device 100 may include both a function in the learning phase and a function in the prediction phase, or may include only one function of the function in the learning phase and the function in the prediction phase. A psychological state sequence prediction device 100 including only the function in the learning phase may be called a learning device. A psychological state sequence prediction device 100 including both the function in the learning phase and the function in the prediction phase may be called a learning device.

Device Configuration in the Learning Phase

As illustrated in FIG. 1, the psychological state sequence prediction device 100 in the learning phase includes a behavior sequence data DB 110, a mood sequence data DB 120, a behavior data preprocessing unit 130, a feature amount extraction unit 140, a mood data preprocessing unit 150, a clustering unit 160, a mood sequence prediction model construction unit 170, a mood sequence prediction model learning unit 180, and a mood sequence prediction model DB 190. Note that the mood sequence prediction model learning unit 180 may be called the "learning unit".

In the psychological state sequence prediction device 100 in the learning phase, the information in the behavior sequence data DB 110 and the information in the mood sequence data DB 120 are used, to output unique parameters constituting a mood sequence prediction model to the mood sequence prediction model DB 190.

Here, the behavior sequence data DB 110 and the mood sequence data DB 120 are constructed beforehand so as to be associated with each other by data recording date and time information. The mood sequence data DB 120 also stores two kinds of numerical values representing the mood of a user at a time when the user makes a self-report. The two kinds of numerical values are Valence and Arousal. Here, Valence indicates the degree of positiveness and negativity of the emotion at that time, and Arousal indicates the degree of excitement in the emotion.

The mood data formed in this manner can be answered by the user using a known technology such as Photographic Affect Meter (PAM) (Non Patent Literature 4), for example. As for the process of constructing the mood sequence data DB 120, results of self-evaluation of moods are input by the subject user, for example, and the input results are stored into a DB.

Note that the use of Valence and Arousal as numerical values indicating a mood is an example. Numerical values other than these values may be used as numerical values indicating moods. Also, a "mood" is an example of a "psychological state".

Device Configuration in the Prediction Phase

As illustrated in FIG. 2, the psychological state sequence prediction device 100 in the prediction phase includes the behavior data preprocessing unit 130, the feature amount extraction unit 140, the mood data preprocessing unit 150, the mood sequence prediction model DB 190, and a mood sequence prediction unit 200. The mood sequence prediction unit 200 may be called the "prediction unit".

The psychological state sequence prediction device 100 in the prediction phase outputs a future mood sequence as a result of prediction from input past behavior sequence data and past mood sequence data.

Example Operation of the Device

In the description below, an operation of the psychological state sequence prediction device 100 having the configuration described above is explained in detail. In the description below, each operation in the learning phase and in the prediction phase is explained.

Learning Phase

Figure 3:
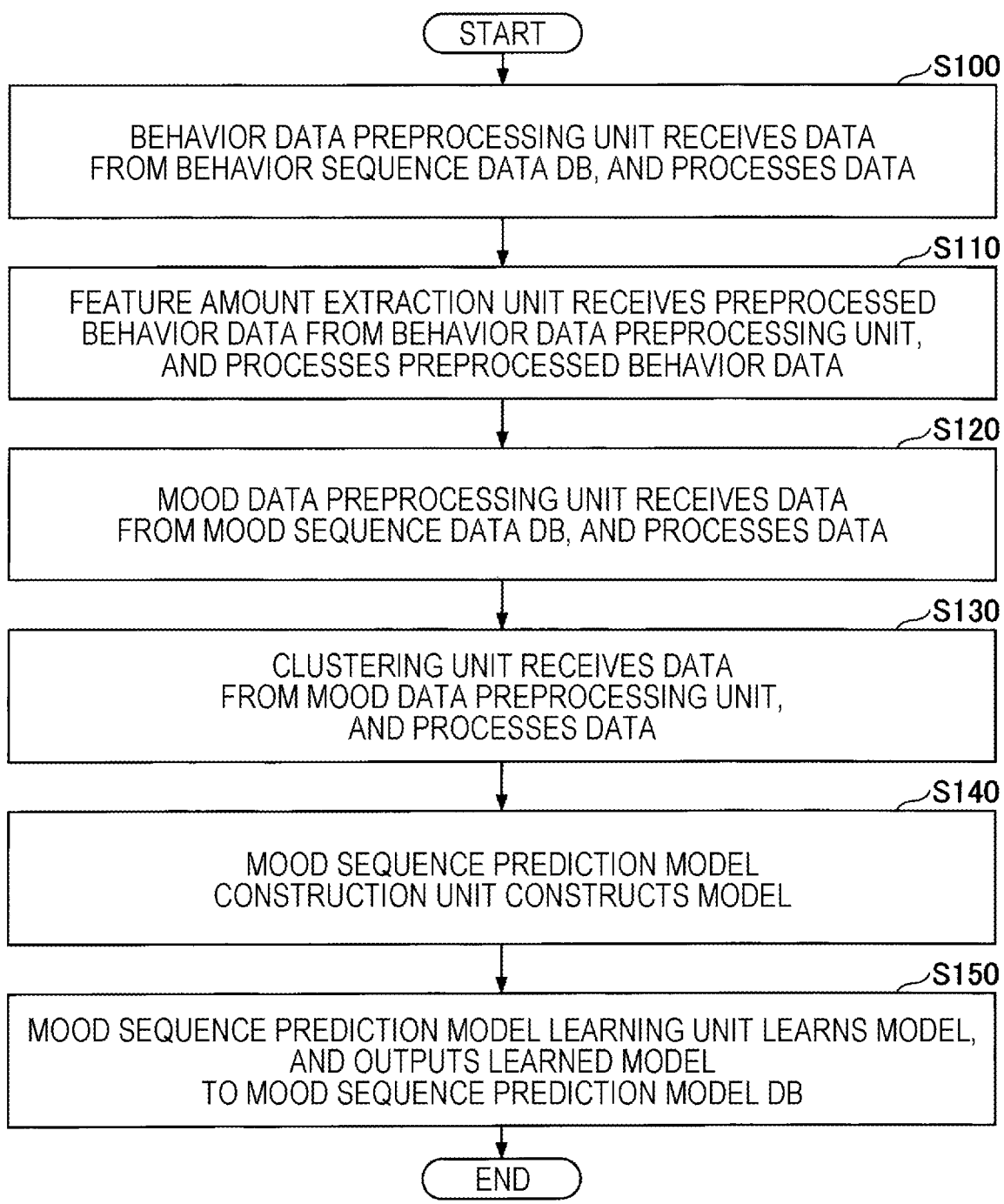
FIG. 3 is a flowchart for explaining an operation of a psychological state sequence prediction device.

FIG. 3 is a flowchart illustrating an operation of the psychological state sequence prediction device 100 in the learning phase. In the description below, the operation of the psychological state sequence prediction device 100 in the learning phase is explained with reference to the flowchart in FIG. 3.

Step 100) The behavior data preprocessing unit 130 receives data from the behavior sequence data DB 110, and processes the data. This process will be described later in detail. FIG. 5 illustrates an example of the data storage format of the behavior sequence data DB 110. As illustrated in FIG. 5, behavior data is recorded, together with time information, in the form of numerical values, times, character strings, and the like in columns showing the respective behaviors (such as walking, exercise, and conversation).

Step 110) The feature amount extraction unit 140 receives the preprocessed data from the behavior data preprocessing unit 130, and processes the preprocessed data. This process will be described later in detail. FIG. 6 illustrates an example of feature vector data obtained as an output of the feature amount extraction unit 140.

Step 120) The mood data preprocessing unit 150 receives data from the mood sequence data DB 120, and processes the data. This process will be described later in detail. FIG. 7 illustrates an example of the data storage format of the mood sequence data DB 120. Mood data is recorded as scores of Valence and Arousal, together with information about the dates and times when the user made self-reports.

FIG. 8 illustrates an example of preprocessed mood data obtained as an output of the mood data preprocessing unit 150.

Step 130) The clustering unit 160 receives the data from the mood data preprocessing unit 150, and processes the data. This process will be described later in detail.

Step 140) The mood sequence prediction model construction unit 170 constructs a model. This process will be described later in detail.

Step 150) The mood sequence prediction model learning unit 180 receives the feature vector data from the feature amount extraction unit 140, receives the preprocessed mood data from the mood data preprocessing unit 150, receives parameters from the clustering unit 160, receives and learns the model from the mood sequence prediction model construction unit 170, and outputs the learned model to the mood sequence prediction model DB 190.

Prediction Phase

Figure 4:
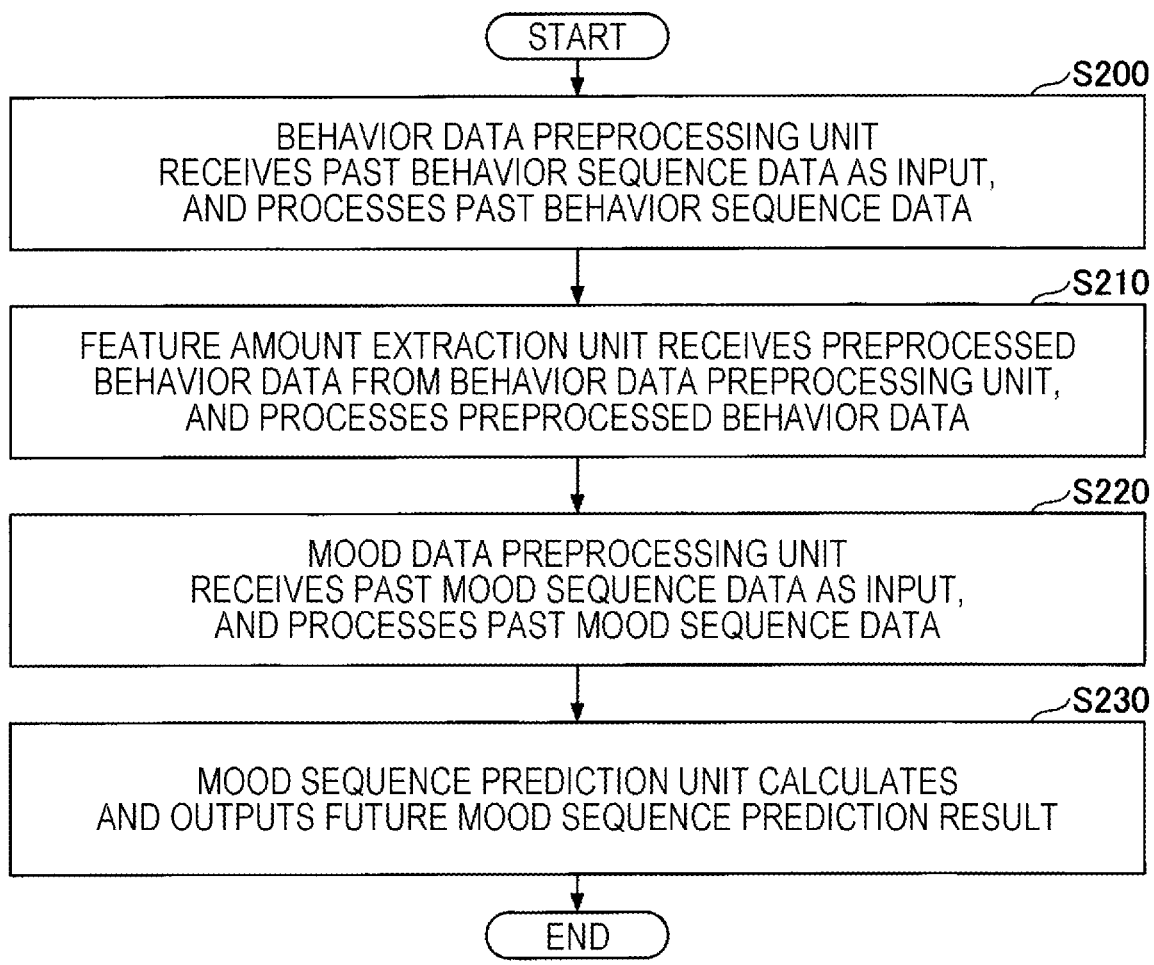
FIG. 4 is a flowchart for explaining an operation of a psychological state sequence prediction device.

FIG. 4 is a flowchart illustrating an operation of the psychological state sequence prediction device 100 in the prediction phase. In the description below, the operation of the psychological state sequence prediction device 100 in the prediction phase is explained with reference to the flowchart in FIG. 4.

Step 200) The behavior data preprocessing unit 130 receives past behavior sequence data as an input, and processes the past behavior sequence data.

Step 210) The feature amount extraction unit 140 receives the preprocessed behavior data from the behavior data preprocessing unit 130, and processes the preprocessed behavior data.

Step 220) The mood data preprocessing unit 150 receives past mood sequence data as an input, and processes the past mood sequence data.

Step 230) The mood sequence prediction unit 200 receives the feature vector data from the feature amount extraction unit 140, receives the preprocessed mood data from the mood data preprocessing unit 150, receives the learned model from the mood sequence prediction model DB 190, calculates a future mood sequence prediction result, and outputs the future mood sequence prediction result. The mood sequence prediction unit 200 may output the above-mentioned received data, together with the future mood sequence prediction result.

Specific Operation of Each Unit

In the description below, an operation of each component in the psychological state sequence prediction device 100 is explained in detail.

Behavior Data Preprocessing Unit 130

Figure 9:
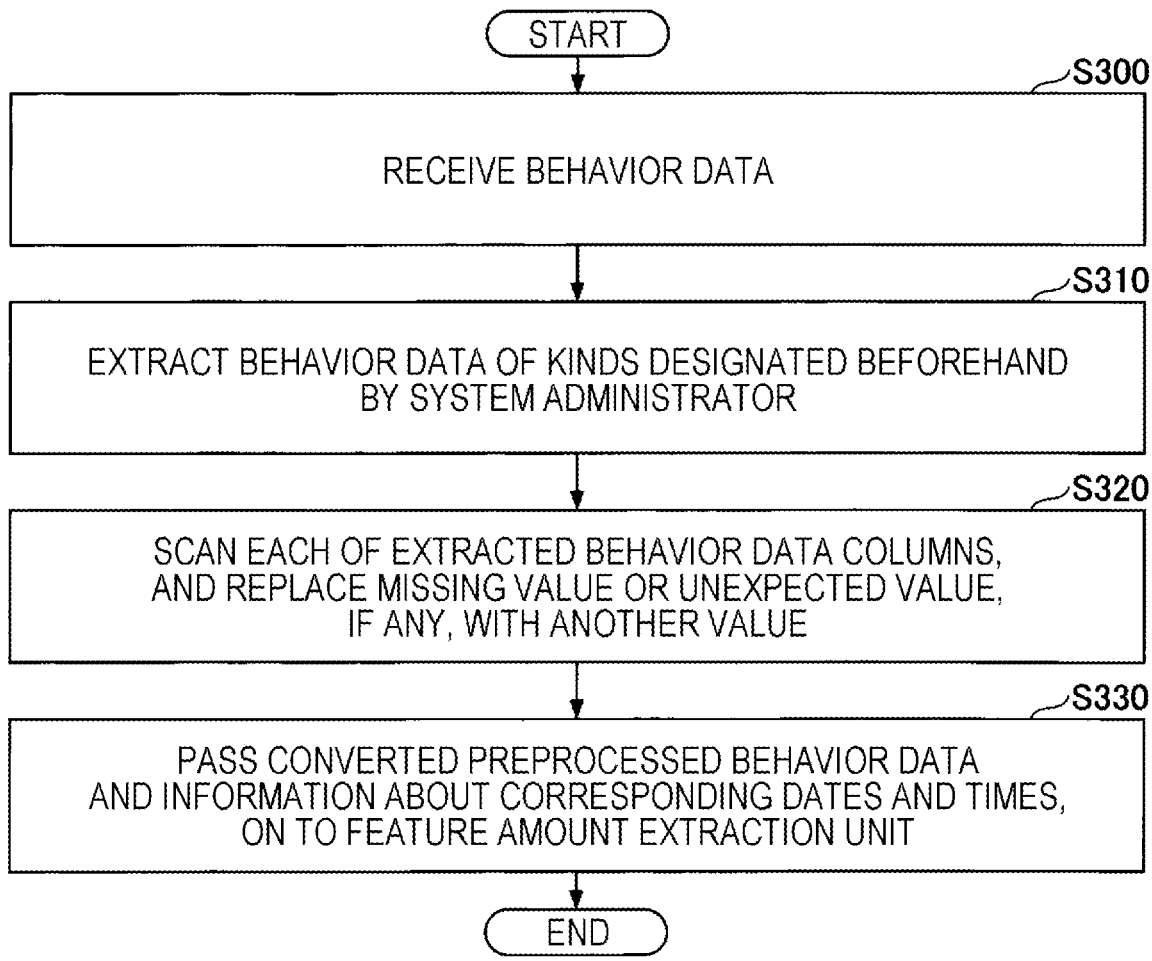
FIG. 9 is a flowchart for explaining an operation of a behavior data preprocessing unit.

FIG. 9 is a flowchart illustrating an operation of the behavior data preprocessing unit 130 in the present embodiment. In the description below, an operation of the behavior data preprocessing unit 130 is explained with reference to the flowchart in FIG. 9.

Step 300) In the case of the learning phase, the behavior data preprocessing unit 130 receives behavior sequence data from the behavior sequence data DB 110. In the case of the prediction phase, the behavior data preprocessing unit 130 receives behavior sequence data as an input.

Step 310) The behavior data preprocessing unit 130 extracts the behavior data (columns) of kinds designated beforehand by the system administrator. For example, the column names of the behavior data to be extracted are defined, and the data in the columns matching the column names are extracted.

Step 320) The behavior data preprocessing unit 130 scans each of the extracted behavior data columns. In a case where there is a missing value or an unexpected value, the behavior data preprocessing unit 130 replaces the missing value or the unexpected value with another value. For example, in the case of numerical data, the mean value of the corresponding column or "0" is inserted. In the case of character string data, a character string indicating that a value is missing is inserted.

Step 330) The behavior data preprocessing unit 130 passes the converted preprocessed behavior data, and information about the corresponding dates and times, on to the feature amount extraction unit 140.

Feature Amount Extraction Unit 140

Figure 10:
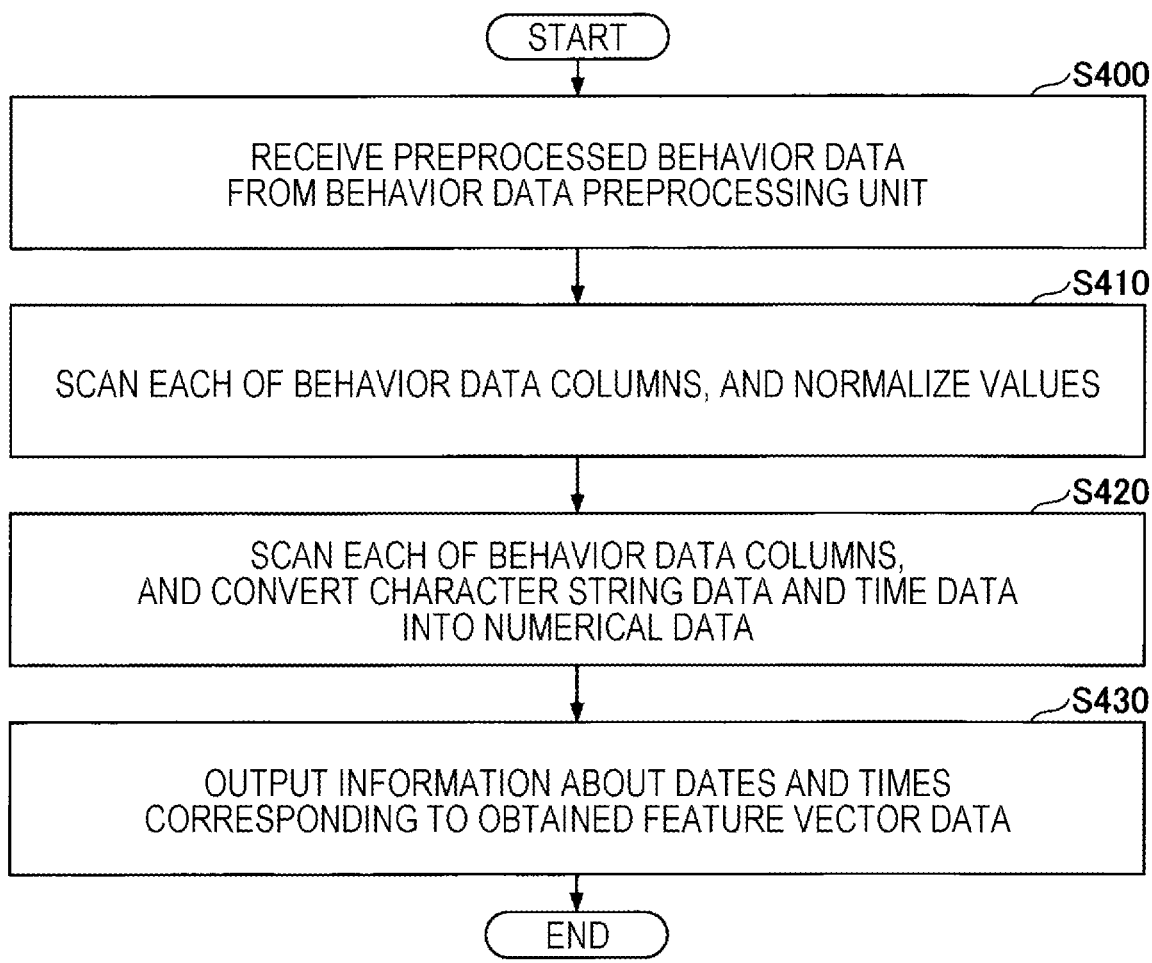
FIG. 10 is a flowchart for explaining an operation of a feature amount extraction unit.

FIG. 10 is a flowchart illustrating an operation of the feature amount extraction unit 140 in the present embodiment. In the description below, an operation of the feature amount extraction unit 140 is explained with reference to the flowchart in FIG. 10.

Step 400) The feature amount extraction unit 140 receives preprocessed behavior data from the behavior data preprocessing unit 130.

Step 410) The feature amount extraction unit 140 scans each of the behavior data columns, and normalizes the values. For example, in the case of numerical data, the data is normalized so that the mean value becomes "0", and the standard deviation becomes "1". In the case of character string data, the number of times the same value appears in the entire data is counted and substituted.

Step 420) The feature amount extraction unit 140 scans each of the behavior data columns, and converts character string data and time data into numerical data. For example, character string data is converted into one-hot vectors related to the corresponding dimension.

Step 430) In the case of the learning phase, the feature amount extraction unit 140 passes information about the dates and the times corresponding to the obtained feature vector data, on to the mood sequence prediction model learning unit 180. In the case of the prediction phase, the feature amount extraction unit 140 passes the information about the dates and the times corresponding to the obtained feature vector data, on to the mood sequence prediction unit 200.

Mood Data Preprocessing Unit 150

Figure 11:
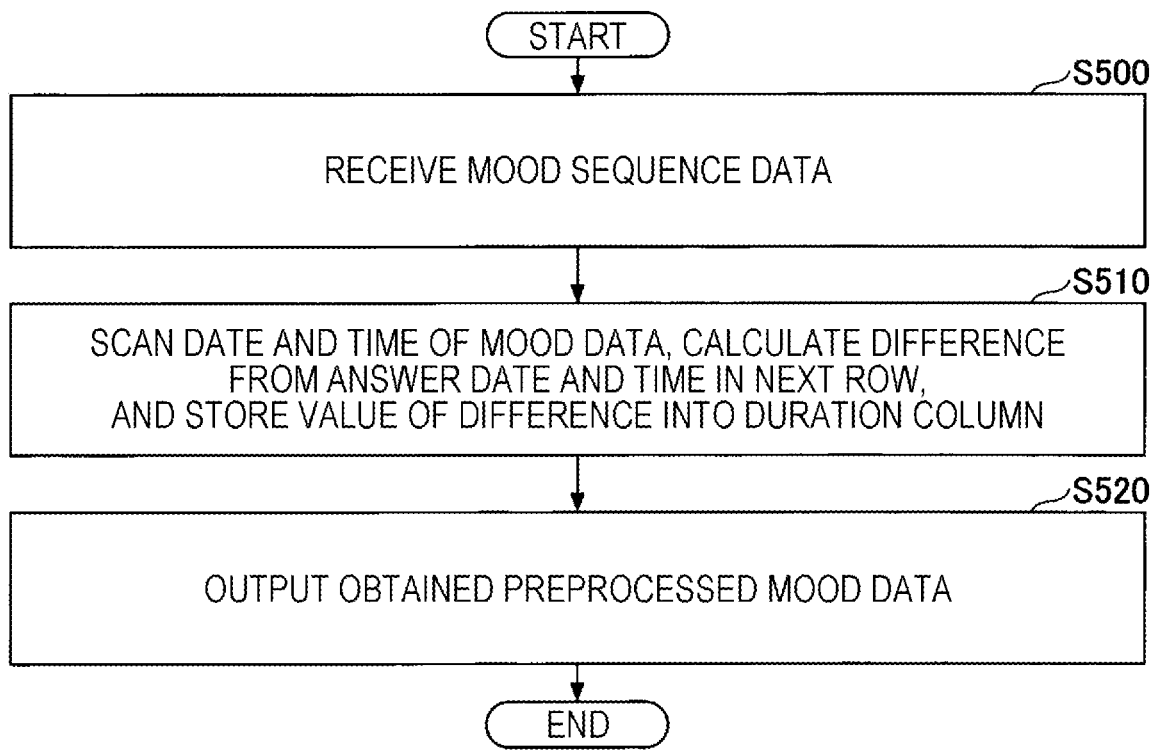
FIG. 11 is a flowchart for explaining an operation of a mood data preprocessing unit.

FIG. 11 is a flowchart illustrating an operation of the mood data preprocessing unit 150 in the present embodiment. In the description below, an operation of the mood data preprocessing unit 150 is explained with reference to the flowchart in FIG. 11.

Step 500) In the case of the learning phase, the mood data preprocessing unit 150 receives mood sequence data from the mood sequence data DB 120. In the case of the prediction phase, the mood data preprocessing unit 150 receives mood sequence data as an input.

Step 510) The mood data preprocessing unit 150 scans the date and time of the mood data, calculates the difference from the answer date and time in the next row, and stores the value into a duration column. For example, in the example illustrated in FIG. 8, the difference between the answer date and time of data ID 1 and the answer date and time of data ID 2 is three hours, and therefore, "3.0 H" is stored into the duration column of data ID 1.

Step 520) In the case of the learning phase, the mood data preprocessing unit 150 passes the obtained preprocessed mood data on to the mood sequence prediction model learning unit 180 and the clustering unit 160. In the case of the prediction phase, the mood data preprocessing unit 150 passes the obtained preprocessed mood data only on to the mood sequence prediction unit 200.

Clustering Unit 160

Figure 12:
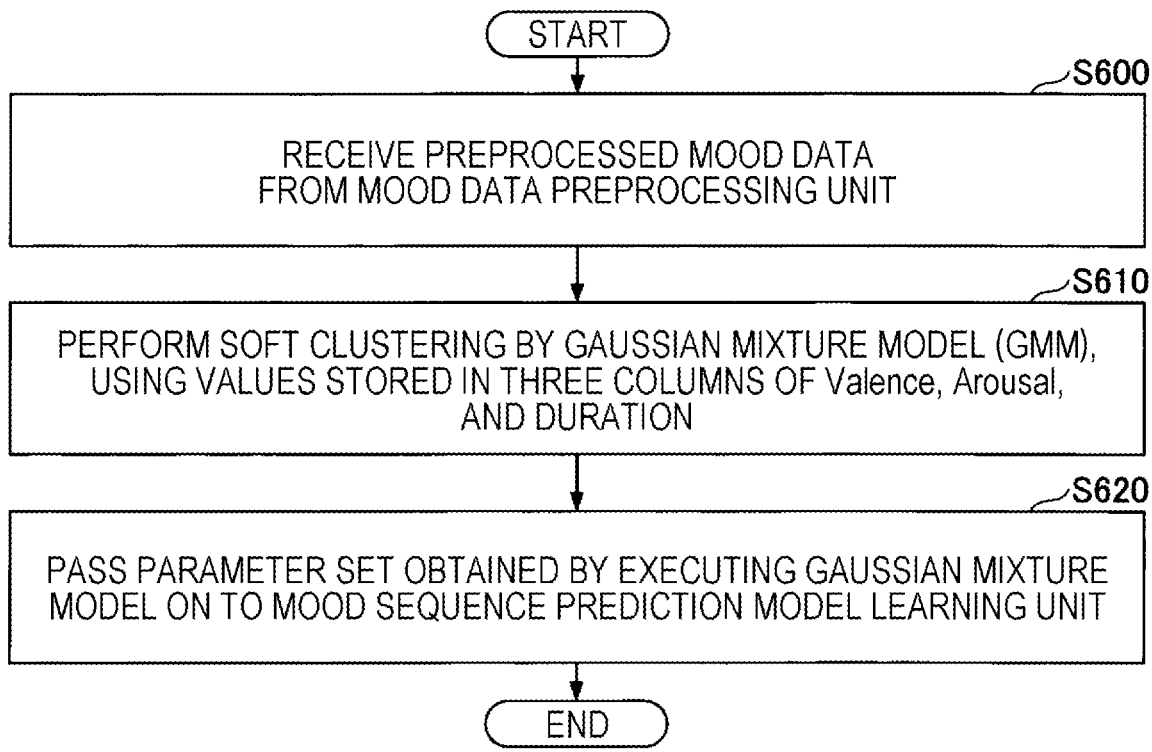
FIG. 12 is a flowchart for explaining an operation of a clustering unit.

FIG. 12 is a flowchart illustrating an operation of the clustering unit 160 in the present embodiment. In the description below, an operation of the clustering unit 160 is explained with reference to the flowchart in FIG. 12.

Step 600) The clustering unit 160 receives preprocessed mood data from the mood data preprocessing unit 150.

Step 610) The clustering unit 160 performs soft clustering by a Gaussian Mixture Model (GMM), using the values stored in the three columns of Valence, Arousal, and duration. The gaussian mixture model may be learned by a known technology such as an EM algorithm. Further, a component number K, which is a hyperparameter of the gaussian mixture model, is set beforehand by the system administrator.

Step 620) The clustering unit 160 passes the parameter set obtained by executing the gaussian mixture model, on to the mood sequence prediction model learning unit 180. The parameter set includes the items shown below.

Mean values of Valences, Arousals, and durations of each component k: $\mu_{v,k}$, $\mu_{a,k}$, and $\mu_{d,k}$ Variances of Valences, Arousals, and durations of each component k: $\sigma_{v,k}$, $\sigma_{a,k}$, and $\sigma_{d,k}$ Correlations between Valences and Arousals, between Valences and durations, and between Arousals and durations of each component: $\rho_{va,k}$, $\rho_{vd,k}$, and $\rho_{ad,k}$ Mood Sequence Prediction Model Construction Unit 170

Figure 13:
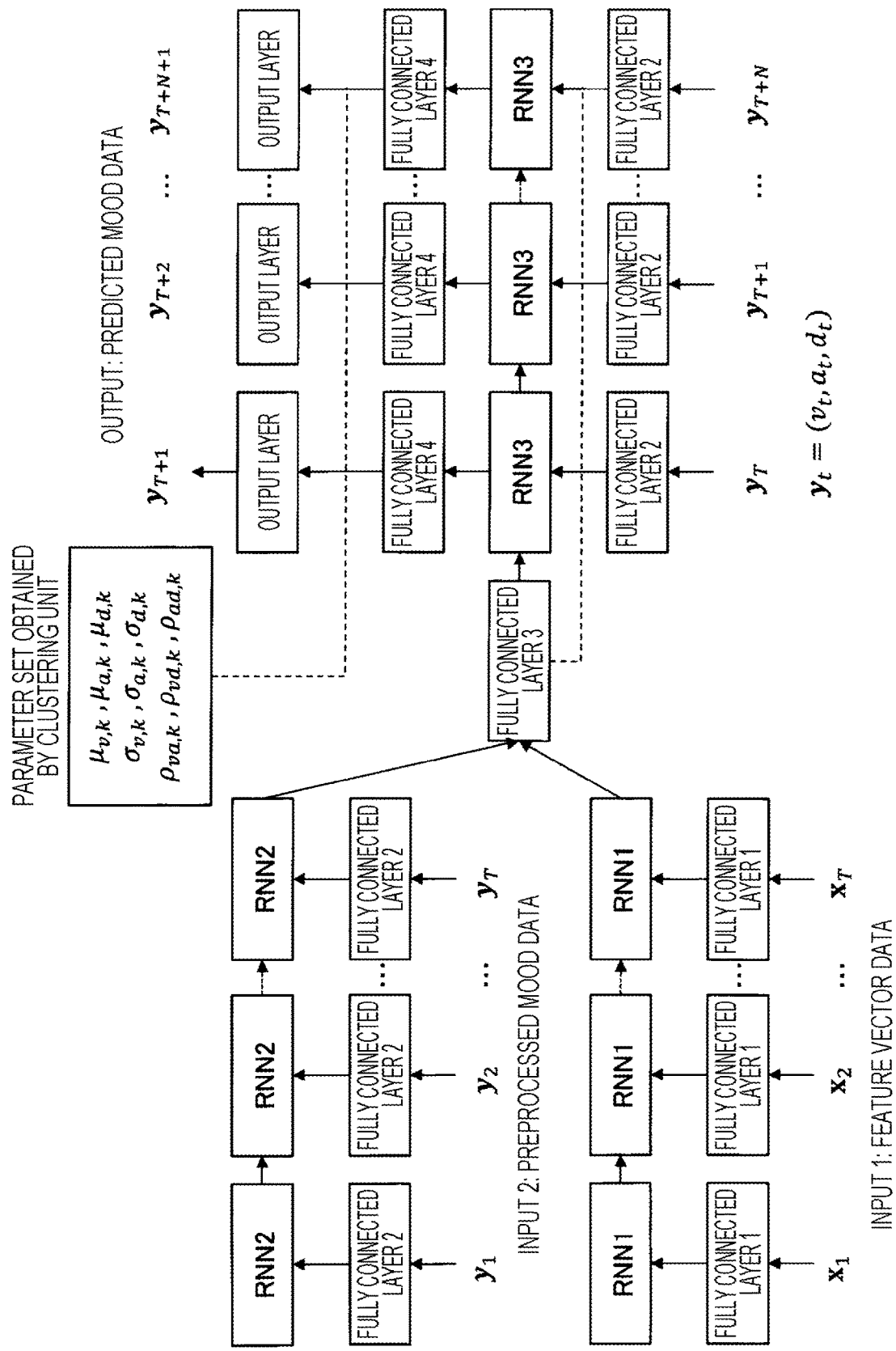
FIG. 13 is a diagram illustrating an example of a DNN constructed by a behavior sequence prediction model construction unit.

FIG. 13 illustrates an example structure of a DNN constructed by the mood sequence prediction model construction unit 170 in the present embodiment. The feature vector data (input 1) and the preprocessed mood sequence data (input 2) at the corresponding time, and the parameter set obtained by the clustering unit 160 are received as inputs, and a future mood sequence of the user is obtained as an output. As illustrated in FIG. 13, the network of this DNN includes the units described below.

The first one is a fully connected layer 1 that extracts more abstract features from feature vector data. Here, after an input is converted by the fully connected layer, the feature amount of the input is subjected to nonlinear conversion with a sigmoid function, a ReLu function, or the like, for example, to obtain a feature vector. This processing is sequentially repeated for the feature vector data provided as time-series data.

The second one is an RNN 1 that further abstracts an abstracted feature vector as sequence data, and is implemented by a known technology such as Long-Short Term Memory (LSTM), for example. Specifically, sequence data is sequentially received, and a nonlinear transform is repeatedly performed, with the past abstracted information being taken into consideration.

The third one is a fully connected layer 2 that extracts more abstract features from preprocessed mood data. Here, processing similar to that performed by the fully connected layer 1 is performed, to obtain a feature vector. This processing is sequentially repeated for the preprocessed mood data provided as time-series data.

The fourth one is an RNN 2 that further abstracts an abstracted feature vector as sequence data, and performs processing by a known technology like the RNN 1, to obtain a feature vector.

The fifth one is a fully connected layer 3 that combines two types of feature vectors obtained by the processing performed by the RNN 1 and the RNN 2 up to the final time in the time-series data into one feature vector, and extracts a new feature vector. Here, processing similar to that performed by the fully connected layer 1 is performed, to obtain a feature vector.

The sixth one is an RNN 3 that is complexed to sequentially obtain mood sequence prediction results. Here, the feature vector obtained by the fully connected layer 3, and the feature vector obtained through the fully connected layer 2 for the mood data at the time immediately before the current prediction target time are received as inputs and are processed, so that a new feature vector is extracted.

The seventh one is a fully connected layer 4 for calculating, from the feature vector obtained by the RNN 3, a probability $\pi_k$ of belonging to each component (a set of mean values, variances, correlations) obtained by the clustering unit 160. Here, after the feature vector is converted into the dimension number corresponding to the component number by the fully connected layer, processing is performed so that the total value of the values in all dimensions becomes 1.0, using a Softmax function or the like.

The eighth one is an output layer that outputs mood data from a three-dimensional normal distribution, using the belonging probability $\pi_k$ obtained by the fully connected layer 4 and the parameter set of each component. This output layer is only enabled in the prediction phase. As for the output method implemented by the output layer, after an index is randomly selected from a K-dimensional multinomial distribution on the basis of the value of the belonging probability $\pi_k$ ($1 \leq k \leq K$), for example, the mean values ($\mu_{v,k}$, $\mu_{a,k}$, and $\mu_{d,k}$), the variances ($\sigma_{v,k}$, $\sigma_{a,k}$, and $\sigma_{d,k}$), and the correlations ($\rho_{va,k}$, $\rho_{vd,k}$, and $\rho_{ad,k}$) associated with the index are obtained. On the basis of these values, Valence, Arousal, and duration are sampled from a three-dimensional (Valence, Arousal, and duration) normal distribution.

Mood Sequence Prediction Model Learning Unit 180

Figure 14:
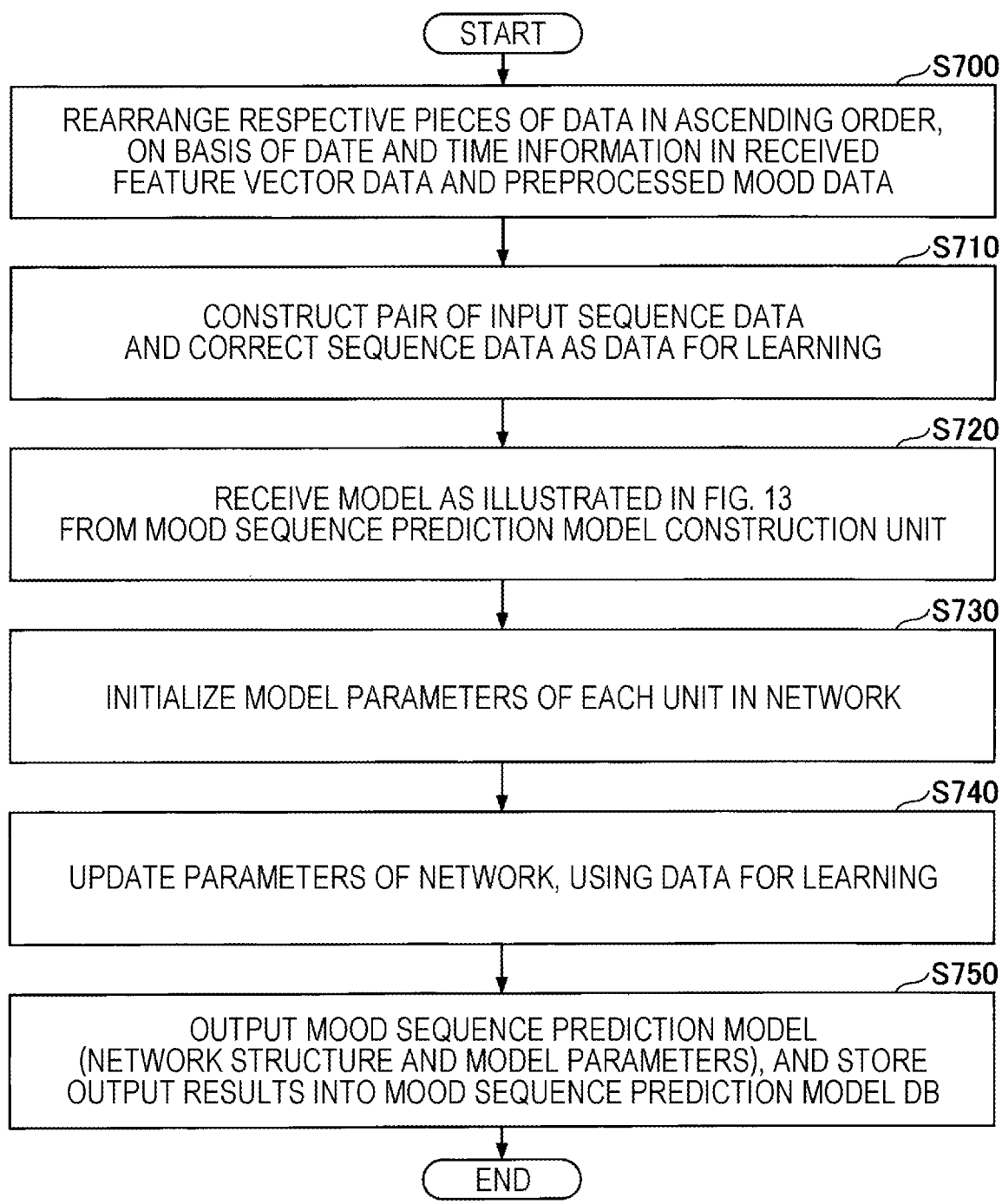
FIG. 14 is a flowchart for explaining an operation of a mood sequence prediction model learning unit.

FIG. 14 is a flowchart illustrating an operation of the mood sequence prediction model learning unit 180 in the present embodiment. In the description below, an operation of the mood sequence prediction model learning unit 180 is explained with reference to the flowchart in FIG. 14.

Step 700) The mood sequence prediction model learning unit 180 rearranges the respective pieces of the data in ascending order, on the basis of the date and time information in the received feature vector data and preprocessed mood data.

Step 710) The mood sequence prediction model learning unit 180 constructs a pair of input sequence data and correct sequence data as data for learning.

For example, when the window size of the input sequence data is T, T pieces of preprocessed mood data are sequentially extracted. The date and time information in the respective pieces of the input sequence data is searched for the minimum time and the maximum time, and the corresponding feature vector data between the times is extracted. The preprocessed mood data and the feature vector data are the input sequence data. When the window size of the correct sequence data is N, T+N pieces of preprocessed mood data are extracted from the index number T in the mood sequence data. In this manner, a pair of input sequence data and correct sequence data is created.

This processing is performed while the window is shifted by W from the head of the preprocessed mood data, and a set of pairs of input sequence data and correct sequence data is constructed, and is used as the learning data.

Step 720) The mood sequence prediction model learning unit 180 receives a model as illustrated in FIG. 13 from the mood sequence prediction model construction unit 170.

Step 730) The mood sequence prediction model learning unit 180 initializes the model parameters of each unit in the network. For example, initialization is performed with a random number from 0 to 1.

Step 740) The mood sequence prediction model learning unit 180 updates the parameters of the network, using the data for learning. Specifically, the parameters of the network are learned so that the correct sequence data can be correctly predicted from the input sequence data. Here, the log likelihood for output sequence data is calculated using the belonging probability πk obtained by the fully connected layer 4 of the network and the parameter set obtained by the clustering unit 160, and the network can be learned through the log likelihood by a known technology such as an error back propagation algorithm. An expression of the likelihood calculation is obtained as shown below.

$$LogLikelihood = -\frac{1}{N}\sum_{n=1}^{N}\log\left(\sum_{k=1}^{K}\pi_{n,k}\mathcal{N}\left(v_n, a_n, d_n \middle| \mu_k, \sum_k\right)\right) \quad \text{[Expression 1]}$$

In the above expression, N represents the size of the output sequence data, K represents the number of components in the clustering unit 160, and $v_n$, $a_n$, and $d_n$ represent Valence, Arousal, and duration of each time step in the correct sequence data. Further, $\mu_k$ and $\Sigma_x$ represent the mean vector and the covariance matrix of each component k formed as shown below.

$$\mu_k = \{\mu_{v,k}, \mu_{a,k}, \mu_{d,k}\} \quad \text{[Expression 2]}$$

$$\sum_k = \begin{bmatrix} \sigma_{v,k}^2 & \rho_{va,k}\sigma_{v,k}\sigma_{a,k} & \rho_{vd,k}\sigma_{v,k}\sigma_{d,k} \\ \rho_{va,k}\sigma_{a,k}\sigma_{v,k} & \sigma_{a,k}^2 & \rho_{ad,k}\sigma_{a,k}\sigma_{d,k} \\ \rho_{vd,k}\sigma_{d,k}\sigma_{v,k} & \rho_{ad,k}\sigma_{d,k}\sigma_{a,k} & \sigma_{d,k}^2 \end{bmatrix}$$

Step 750) The mood sequence prediction model learning unit 180 outputs a mood sequence prediction model (the network structure and the model parameters), and stores the output results into the mood sequence prediction model DB 190. FIG. 15 illustrates an example of the model parameters. In each unit, parameters are stored as a matrix or a vector. Also, the fully connected layer 4 is designed so that the same number of dimensions as the number of components in the clustering unit 160 is output. The output layer holds the values of the parameter set obtained by the clustering unit 160, and is designed so that Valence, Arousal, and duration correspond to one another.

Mood Sequence Prediction Unit 200

Figure 16:
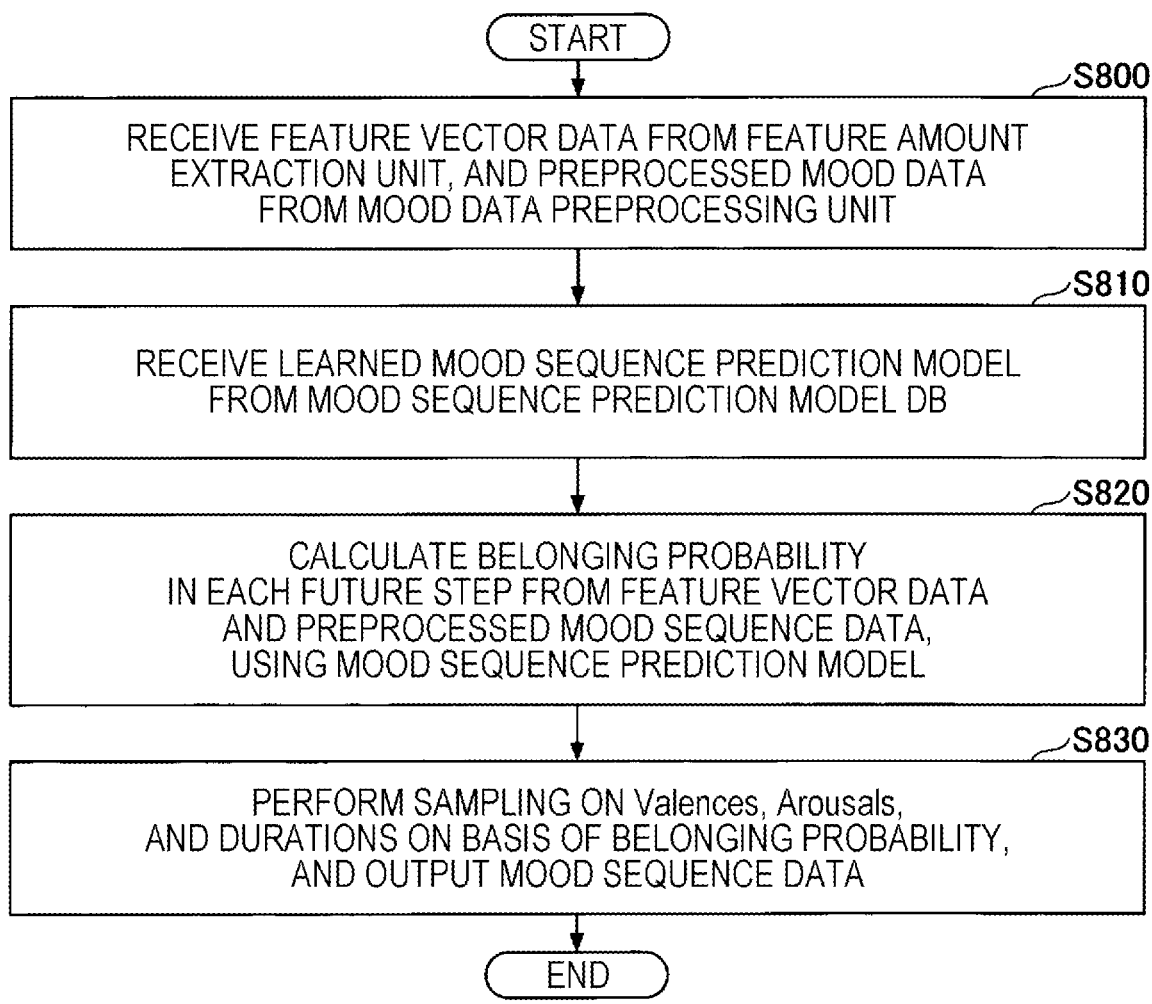
FIG. 16 is a flowchart for explaining an operation of a mood sequence prediction unit.

FIG. 16 is a flowchart illustrating an operation of the mood sequence prediction unit 200 in the present embodiment. In the description below, an operation of the mood sequence prediction unit 200 is explained with reference to the flowchart in FIG. 16.

Step 800) The mood sequence prediction unit 200 receives feature vector data from the feature amount extraction unit 140, and receives preprocessed mood data from the mood data preprocessing unit 150.

Step 810) The mood sequence prediction unit 200 receives a learned mood sequence prediction model from the mood sequence prediction model DB 190.

Step 820) Using the mood sequence prediction model, the mood sequence prediction unit 200 calculates a belonging probability Ix in each future step from the feature vector data and the preprocessed mood sequence data.

Step 830) The mood sequence prediction unit 200 performs sampling on Valences, Arousals, and durations on the basis of the belonging probability $\pi_k$, and outputs mood sequence data.

Example Hardware Configuration

The psychological state sequence prediction device 100 including both the function in the learning phase and the function in the prediction phase, the psychological state sequence prediction device 100 including only the function in the learning phase, and the psychological state sequence prediction device 100 including only the function in the prediction phase can be formed with a computer that is made to execute a program, for example, in any case. This computer may be a physical computer, or may be a virtual machine in a cloud.

Specifically, the psychological state sequence prediction device 100 can be implemented by executing a program corresponding to the processing to be performed in the psychological state sequence prediction device 100, using hardware resources such as a CPU and a memory installed in the computer. The above program can be recorded in a computer-readable recording medium (such as a portable memory), and be stored or distributed. Further, the above program can also be provided through a network such as the Internet or electronic mail.

Figure 17:
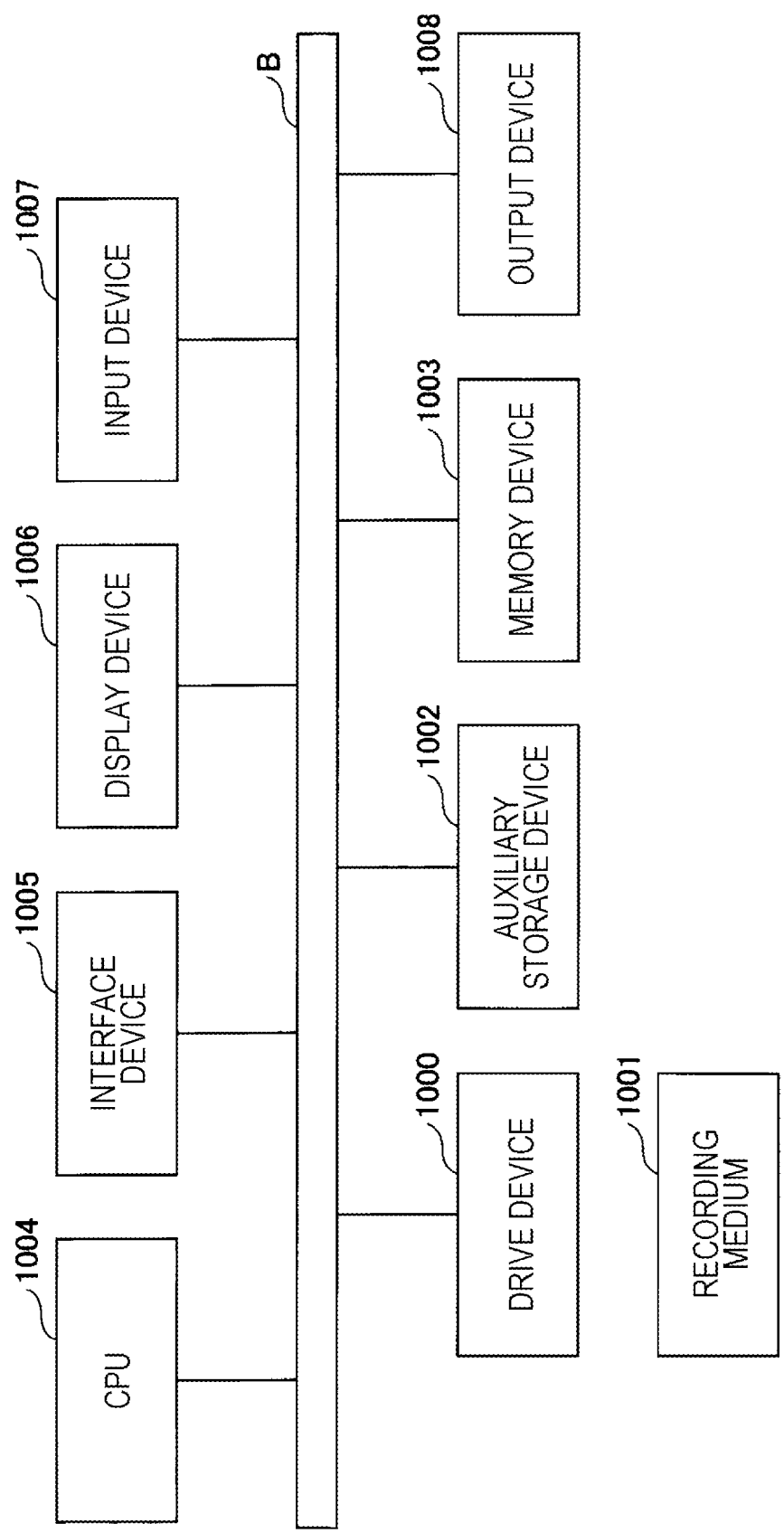
FIG. 17 is a diagram illustrating an example hardware configuration of a device.

FIG. 17 is a diagram illustrating an example hardware configuration of the above computer. The computer in FIG. 17 includes a drive device 1000, an auxiliary storage device 1002, a memory device 1003, a CPU 1004, an interface device 1005, a display device 1006, an input device 1007, and an output device 1008, which are connected to one another by a bus BS. Note that some of these devices are not necessarily included. For example, in a case where display is not to be performed, the display device 1006 may not be included.

The program for performing the processing in the computer is provided through a recording medium 1001 such as a CD-ROM or a memory card, for example. When the recording medium 1001 storing the program is set in the drive device 1000, the program is installed from the recording medium 1001 into the auxiliary storage device 1002 via the drive device 1000. However, the program is not necessarily installed from the recording medium 1001, and may be downloaded from another computer via a network. The auxiliary storage device 1002 stores the installed program, and also stores necessary files, data, and the like.

In a case where an instruction to start the program is issued, the memory device 1003 reads the program from the auxiliary storage device 1002, and stores the program. The CPU 1004 implements the functions related to the psychological state sequence prediction device 100, according to the program stored in the memory device 1003. The interface device 1005 is used as an interface for connecting to a network. The display device 1006 displays a graphical user interface (GUI) or the like according to the program. The input device 1007 includes a keyboard and mouse, buttons, a touch panel, or the like, and is used to input various operation instructions. The output device 1008 outputs a calculation result.

SUMMARY OF THE EMBODIMENT

In the psychological state sequence prediction device 100 according to the present embodiment described above, in the learning phase, the behavior data preprocessing unit 130 processes the data in the behavior sequence data DB, and the feature amount extraction unit 140 processes the preprocessed behavior data. Also, the mood data preprocessing unit 150 processes the data in the mood sequence data DB 120, and the clustering unit 160 processes the preprocessed mood data.

Also, in the learning phase, the mood sequence prediction model construction unit 170 constructs a model that can handle feature vector data and mood sequence data based on behavior sequence data. The mood sequence prediction model learning unit 180 learns and optimizes the mood sequence prediction model from the behavior sequence data and the mood sequence data, and outputs the model to the mood sequence prediction model DB 190.

In the prediction phase, the behavior data preprocessing unit 130 processes input behavior data, and the feature amount extraction unit 140 processes the preprocessed behavior data. The mood data preprocessing unit 150 processes input mood data. Using a learned model, the mood sequence prediction unit 200 calculates and outputs a future mood sequence, together with the duration of each mood, from the feature vector data and the mood data.

As for more specific processing, the behavior data preprocessing unit 130 and the feature amount extraction unit 140 perform behavior data normalization, character string data conversion, and the like, so that the DNN can readily handle the data. Further, the clustering unit 160 learns the tendency of the user's mood from the preprocessed mood data as a plurality of components including average values, variances, and correlations, and passes the obtained parameter set to the mood sequence prediction model learning unit 180.

The mood sequence prediction model learning unit 180 learns the network, using the parameter set obtained by the clustering unit 160. An output layer in the mood sequence prediction model uses the parameter set obtained by the clustering unit 160, to output the correlations among Valences, Arousals, and durations.

Effects of the Embodiment

With the psychological state sequence prediction device 100 having the functions as described above, it is possible to predict a user's future mood sequence that cannot be predicted by conventional technologies, together with its duration, by preprocessing mood sequence data, calculating a mood duration, and learning a mood sequence prediction model in conjunction with a feature vector obtained from the behavior sequence data. A prediction result, together with a mood duration, is presented in this manner, so that the prediction result can be used in analyzing influences on future mental health.

Further, as the mean value, the variances, and the correlations of the Valence and Arousal constituting a mood, and the durations are captured for each user, a future mood sequence can be predicted with high accuracy.

Also, as the mean values, the variances, and the correlations of the Valences, the Arousals, and the durations are learned in a neural network, it is possible to predict a future mood sequence with high accuracy even from a small amount of training data, by calculating those values beforehand with the clustering unit.

Supplementary Notes

The present specification discloses at least a learning device, a psychological state sequence prediction device, a learning method, a psychological state sequence prediction method, and a program of the items described below.

(Item 1)
  A learning device including:
    a psychological state data preprocessing unit that calculates a duration of a psychological state from psychological state sequence data, and generates preprocessed psychological state sequence data including the psychological state and the duration; and
    a learning unit that learns a psychological state sequence prediction model, using input sequence data including behavior sequence data and the preprocessed psychological state sequence data, and correct sequence data that is preprocessed psychological state sequence data at a time later than the input sequence data.

(Item 2)
  The learning device according to Item 1, further including
    a clustering unit that performs soft clustering on the preprocessed psychological state sequence data obtained by the psychological state data preprocessing unit, and outputs a parameter set related to the psychological state and the duration of each component,
    in which the learning unit learns the psychological state sequence prediction model from a probability of belonging to each component and the parameter set, the probability of belonging being obtained by the psychological state sequence prediction model from the input sequence data.

(Item 3)
  A psychological state sequence prediction device including:
    a psychological state data preprocessing unit that calculates a duration of a psychological state from psychological state sequence data, and generates preprocessed psychological state sequence data including the psychological state and the duration; and
    a prediction unit that predicts a future psychological state and a duration thereof, by inputting past behavior sequence data and past preprocessed psychological state sequence data obtained by the psychological state data preprocessing unit, to a psychological state sequence prediction model learned with use of input sequence data including behavior sequence data and the preprocessed psychological state sequence data, and correct sequence data that is preprocessed psychological state sequence data at a time later than the input sequence data.

(Item 4)
  The psychological state sequence prediction device according to Item 3, in which
    the prediction unit predicts a future psychological state and a duration thereof, on the basis of a parameter set and a probability of belonging to a component, the parameter set being related to a psychological state and a duration of each component obtained by performing soft clustering on the preprocessed psychological state sequence data during learning, the probability of belonging being obtained by the psychological state sequence prediction model.

(Item 5)
  A learning method including:
    a psychological state data preprocessing step of calculating a duration of a psychological state from psychological state sequence data, and generating preprocessed psychological state sequence data including the psychological state and the duration; and
    a learning step of learning a psychological state sequence prediction model, using input sequence data including behavior sequence data and the preprocessed psychological state sequence data, and correct sequence data that is preprocessed psychological state sequence data at a time later than the input sequence data.

(Item 6)

A psychological state sequence prediction method including:
- a psychological state data preprocessing step of calculating a duration of a psychological state from psychological state sequence data, and generating preprocessed psychological state sequence data including the psychological state and the duration; and
- a prediction step of predicting a future psychological state and a duration thereof, by inputting past behavior sequence data and past preprocessed psychological state sequence data obtained in the psychological state data preprocessing step, to a psychological state sequence prediction model learned with use of input sequence data including behavior sequence data and the preprocessed psychological state sequence data, and correct sequence data that is preprocessed psychological state sequence data at a time later than the input sequence data.

(Item 7)

A program for causing a computer to function as each unit in the learning device according to Item 1 or 2, or a program for causing a computer to function as each unit in the psychological state sequence prediction device according to Item 3 or 4.

Although the present embodiment has been described so far, the present invention is not limited to such a specific embodiment, and various modifications and changes can be made to it within the scope of the present invention disclosed in the claims.

REFERENCE SIGNS LIST

- 100 psychological state sequence prediction device
- 110 behavior sequence data DB
- 120 mood sequence data DB
- 130 behavior data preprocessing unit
- 140 feature amount extraction unit
- 150 mood data preprocessing unit
- 160 clustering unit
- 170 mood sequence prediction model construction unit
- 180 mood sequence prediction model learning unit
- 190 mood sequence prediction model DB
- 200 mood sequence prediction unit
- 1000 drive device
- 1001 recording medium
- 1002 auxiliary storage device
- 1003 memory device
- 1004 CPU
- 1005 interface device
- 1006 display device
- 1007 input device
- 1009 output device

The invention claimed is:

1. A learning apparatus comprising:
   a memory; and
   a processor configured to execute:
   scanning each of behavior data columns that are extracted from a behavior sequence database,
   replacing a missing value or an unexpected value with another value in a case where there is the missing value or the unexpected value, thereby generating past behavior sequence data;
   calculating a duration of a mental state from mental state sequence data, and generating preprocessed mental state sequence data including the mental state and the duration; and
   learning a mental state sequence prediction model, using input sequence data including the behavior sequence data and the preprocessed mental state sequence data, and correct sequence data that is preprocessed mental state sequence data at a time later than the input sequence data,
   wherein the mental state is defined by mood data including valence and arousal, together with information about dates and times when a user makes self-reports, said valence indicating degree of positiveness and negativity of emotion of the user at that time, and said arousal indicating degree of excitement in the emotion of the user, and
   wherein the processor is further configured to execute:
   calculating the duration of the mental state by calculating a difference of an entry of the mood data and next entry of the mood data.

2. The learning apparatus according to claim 1, wherein the processor is further configured to execute:
   performing soft clustering on the preprocessed mental state sequence data obtained at the generating, and outputting a parameter set related to a mental state and a duration of each component,
   wherein the learning includes learning the mental state sequence prediction model from a probability of belonging to each component and the parameter set, the probability of belonging being obtained by the mental state sequence prediction model from the input sequence data.

3. The learning apparatus according to claim 1, wherein the processor is further configured to execute:
   replacing the missing value or the unexpected value with the another value by inserting the mean value of a corresponding column in the behavior sequence database or "0" in the case of numerical data, and inserting a character string indicating that a value is missing in the case of character string data.

4. A mental state sequence prediction apparatus comprising:
   a memory; and
   a processor configured to execute:
   scanning each of behavior data columns that are extracted from a behavior sequence database,
   replacing a missing value or an unexpected value with another value in a case where there is the missing value or the unexpected value, thereby generating past behavior sequence data;
   calculating a duration of a mental state from mental state sequence data, and generating preprocessed mental state sequence data including the mental state and the duration; and
   predicting a future mental state and a duration of the future mental state, by inputting the past behavior sequence data and past preprocessed mental state sequence data obtained at the generating, to a mental state sequence prediction model learned with use of input sequence data including behavior sequence data and the preprocessed mental state sequence data, and correct sequence data that is preprocessed mental state sequence data at a time later than the input sequence data,
   wherein the mental state is defined by mood data including valence and arousal, together with information about dates and times when a user makes self-reports, said valence indicating degree of positiveness and negativity of emotion of the user at that time, and said arousal indicating degree of excitement in the emotion of the user, and wherein the processor is further configured to execute:

calculating the duration of the mental state by calculating a difference of an entry of the mood data and the next entry of the mood data.

5. The mental state sequence prediction apparatus according to claim 4, wherein the predicting includes predicting a future mental state and a duration of the future mental state, on a basis of a parameter set and a probability of belonging to a component, the parameter set being related to a mental state and a duration of each component, the parameter set being obtained by soft clustering performed on the preprocessed mental state sequence data during learning, the probability of belonging being obtained by the mental state sequence prediction model.

6. A learning method comprising:

scanning each of behavior data columns that are extracted from a behavior sequence database, replacing a missing value or an unexpected value with another value in a case where there is the missing value or the unexpected value, thereby generating behavior sequence data;

calculating a duration of a mental state from mental state sequence data, and generating preprocessed mental state sequence data including the mental state and the duration; and learning a mental state sequence prediction model, using input sequence data including the behavior sequence data and the preprocessed mental state sequence data, and correct sequence data that is preprocessed mental state sequence data at a time later than the input sequence data, wherein the mental state is defined by mood data including valence and arousal, together with information about dates and times when a user makes self-reports, said valence indicating degree of positiveness and negativity of emotion of the user at that time, and said arousal indicating degree of excitement in the emotion of the user, and wherein the processor is further configured to execute:

calculating the duration of the mental state by calculating a difference of an entry of the mood data and the next entry of the mood data.

7. A mental state sequence prediction method comprising:

scanning each of behavior data columns that are extracted from a behavior sequence database, replacing a missing value or an unexpected value with another value in a case where there is the missing value or the unexpected value, thereby generating past behavior sequence data;

calculating a duration of a mental state from mental state sequence data, and generating preprocessed mental state sequence data including the mental state and the duration; and predicting a future mental state and a duration of the future mental state, by inputting past behavior sequence data and past preprocessed mental state sequence data obtained at the generating, to a mental state sequence prediction model learned with use of input sequence data including behavior sequence data and the preprocessed mental state sequence data, and correct sequence data that is preprocessed mental state sequence data at a time later than the input sequence data, wherein the mental state is defined by mood data including valence and arousal, together with information about dates and times when a user makes self-reports, said valence indicating degree of positiveness and negativity of emotion of the user at that time, and said arousal indicating degree of excitement in the emotion of the user, and wherein the processor is further configured to execute:

calculating the duration of the mental state by calculating a difference of an entry of the mood data and the next entry of the mood data.

8. A non-transitory computer-readable recording medium having computer-readable instructions stored thereon, which when executed, cause a computer to function as the learning apparatus according to claim 1.

* * * * *